US00PP23599P2

(12) United States Plant Patent
Hanes

(10) Patent No.: US PP23,599 P2
(45) Date of Patent: May 14, 2013

(54) ***PETUNIA* PLANT NAMED 'PEHY0001'**

(50) Latin Name: *Petunia hybrida*
Varietal Denomination: PEHY0001

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 83 days.

(21) Appl. No.: 13/317,475

(22) Filed: Oct. 19, 2011

(51) Int. Cl.
*A01H 5/00* (2006.01)

(52) U.S. Cl.
USPC ..... Plt./356.1

(58) Field of Classification Search ..... Plt./356.1
See application file for complete search history.

*Primary Examiner* — Annette Para
(74) *Attorney, Agent, or Firm* — Joshua L. Price

(57) ABSTRACT

A new *Petunia* plant named 'PEHY0001' particularly distinguished by the small bold red-purple flowers, good floriferousness, medium green foliage, initially semi-compact and then an outwardly spreading plant habit, and is early to flower.

1 Drawing Sheet

Latin name of the genus and species of the plant claimed: *Petunia hybrida.*

Varietal denomination: 'PEHY0001'.

BACKGROUND OF THE NEW PLANT

The present invention comprises a new *Petunia*, botanically known as *Petunia hybrida*, and hereinafter referred to by the variety name 'PEHY0001'.

'PEHY0001' is a product of a planned breeding program. The new cultivar has small bold red-purple flowers, good floriferousness, medium green foliage, initially semi-compact and then an outwardly spreading plant habit, and is early to flower.

'PEHY0001' originated from a hybridization made in August 2007 in a controlled breeding environment in Gilroy, Calif. The female parent was the proprietary, unpatented plant designated '1789-2', with larger amethyst colored flowers with more expressed veining and more upright plant habit.

The male parent of 'PEHY0001' is a commercially available proprietary variety identified as 'Pic Whit', U.S. Plant Pat. No. 22,182, with white flowers, somewhat more trailing plant habit and is more vigorous. The resultant seed was sown in December 2007.

'PEHY0001' was selected as one flowering plant within the progeny of the stated cross in the March 2008 in a controlled environment in Gilroy, Calif.

The first act of asexual reproduction of 'PEHY0001' was accomplished when vegetative cuttings were propagated from the initial selection in March 2008 in a controlled environment in Gilroy, Calif.

BRIEF SUMMARY OF INVENTION

Horticultural examination of plants grown from cuttings of the plant initiated in March 2008, and continuing thereafter, has demonstrated that the combination of characteristics as herein disclosed for 'PEHY0001' are firmly fixed and are retained through successive generations of asexual reproduction.

'PEHY0001' has not been observed under all possible environmental conditions. The phenotype may vary significantly with variations in environment such as temperature, light intensity and day length.

Plant Breeder's Rights for this cultivar were applied for in Canada on Dec. 17, 2010, #10-7130 and the Community Plant Variety Office on Oct. 15, 2010, #2010/2182. 'PEHY0001' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0001' with colors being as true as possible with an illustration of this type. The photographic drawing shows three flowering plants of the new variety, and a close-up of the flowers.

DETAILED BOTANICAL DESCRIPTION

The aforementioned photographs and were taken in Enkhuizen, The Netherlands in summer 2009 from plants growing in a greenhouse. These plants were growing in 10 inch containers, 3 plants per container, about 13-15 weeks of age.

The plant descriptions and measurements were taken in Gilroy, Calif. in late April 2011 from plants grown in a breeder trial in the greenhouse. Plants were grown in 4.5 inch pots and were approximately 10 weeks of age.

Color references are made to The Royal Horticultural Society Colour Chart (R.H.S.) 2001.

TABLE 1

DIFFERENCES BETWEEN THE NEW VARIETY 'PEHY0001' AND A SIMILAR VARIETY

| | 'PEHY0001' | 'Pic Rossa' (U.S. Plant Pat. No. 21,599) |
|---|---|---|
| Flower color: | Closest RHS N74A | Closest RHS N66B |
| Vigor: | Has more vigor | Has less vigor |
| Plant habit: | More compact | Less compact |

Plant:

*Form, growth and habit.*—Initially semi-compact, to outwardly spreading, vigorous, well branched habit, small foliage, and good floriferiousness.

*Plant height.*—5.0-7.0 cm.

*Plant height (inflorescence included).*—8.0-11.0 cm.

*Plant width.*—45.0-53.0 cm.

Roots:

*Number of days to initiate roots and produce a rooted cutting.*—18-23 days at about 22 degrees C.

*Type.*—Fine, fibrous, free branching.

*Color.*—RHS N155B but whiter.

Foliage:

*Arrangement.*—Alternate, upper leaves sub-opposite.

*Immature, leaf color, upper surface.*—Closest to RHS 137A. Lower surface: Closest to RHS 137C.

*Mature, leaf color, upper surface.*—Closest to RHS 137A. Lower surface: Closest to RHS 137C.

*Length.*—1.9-2.5 cm.

*Width.*—0.9-1.2 cm.

*Shape.*—Elliptical.

*Base shape.*—Attenuate.

*Apex shape.*—Obtuse.

*Margin.*—Entire.

*Texture, upper surface.*—Hirsute; glandular hairs. Lower surface: Hirsute; glandular hairs.

*Color of veins, upper surface.*—Closest to RHS 144B; indistinct in upper portion.

*Color of veins, lower surface.*—Closest to RHS 144B; indistinct in upper portion.

*Petiole color.*—Closest to RHS 144B.

*Length.*—0.15-0.25 cm.

*Diameter.*—0.2 cm.

*Texture.*—Hirsute; glandular hairs.

Stem:

*Color of stem.*—Closest to RHS 143C.

*Length of stem.*—23.0-31.0 cm.

*Diameter.*—0.2 cm.

*Length of internodes.*—0.5-1.4 cm.

*Texture.*—Hirsute, some pilose, glandular hairs.

*Color of peduncle.*—RHS 143C.

*Length of peduncle.*—3.2-4.3 cm.

*Peduncle diameter.*—0.1 cm.

*Texture.*—Hirsute, some pilose, glandular hairs.

Inflorescence:

*Type.*—Flowers appear solitary in upper leaf axis.

*Floret type.*—Funnel-shaped; 5 lobed petals; fused at the base; calyx, 5 deeply lobed sepals.

*Blooming habit.*—Continuous throughout the growing season. Good floriferousness.

*Quantity of inflorescences per plant.*—About 125 plus numerous buds.

*Lastingness of individual blooms on the plant.*—5-7 days.

*Fragrance.*—None.

Bud (just before opening/showing color):

*Color.*—RHS 79C.

*Length.*—1.9-2.2 cm.

*Width.*—0.5 cm.

*Shape.*—Oblong.

Immature inflorescence:

*Diameter.*—2.4-2.9 cm.

*Color, upper surface.*—Closest to RHS N81A but more blue-red with RHS N79A mid-veins. Lower surface: RHS N81C with RHS N81B margins.

Mature inflorescence:

*Floret horizontal diameter.*—3.2-3.5 cm.

*Vertical depth.*—3.5-3.7 cm.

*Petal color, upper surface.*—Closest to RHS N74A with RHS N77A mid-veins. Lower surface: RHS N74C with RHS N74B margins and RHS N77A mid-veins.

*Petal apex shape.*—Slightly retuse.

*Petal base shape.*—Fused.

*Petal margin.*—Entire.

*Waviness of petals.*—Slight.

*Petal lobation.*—Moderate.

*Petal texture, upper surface.*—Papillose. Under surface: Papillose.

*Corolla tube color inside.*—Closest to RHS 86A with RHS N77A mid-veins, and heavily veined with RHS 83B and RHS 83B. Outside: RHS 77B but greyer with RHS N77B mid-veins and RHS N77C veining.

*Corolla tube length.*—2.2-2.5 cm.

*Corolla texture, outside.*—Pilose, glandular hairs. Inside: Papillose

Calyx:

*Color, upper surface.*—RHS 143B. Lower surface: RHS 143B.

*Length.*—0.7-0.9 cm.

*Width.*—0.2 cm.

*Shape.*—Narrowly elliptical.

*Apex shape.*—Obtuse.

*Base.*—Fused.

*Margins.*—Entire.

*Texture, upper surface.*—Glabrous. Lower surface: Hirsute, pilose, glandular hairs.

Reproductive organs:

*Pistil.*—1.

*Length.*—1.7-1.9 cm.

*Style color.*—RHS 144C but slightly lighter hue, with about RHS N186B just below the stigma.

*Style length.*—0.9 cm.

*Stigma color.*—RHS 147C to RHS 147D.

*Ovary color.*—Closest to RHS 143C and slightly darker just below the style.

*Stamens.*—5.

*Color of filaments.*—RHS 145D basally with uppers a shade of RHS N66C or RHS N66D just below the anthers.

*Length filaments.*—1.5-2.0 cm.
*Anther color.*—RHS N187D.
*Anther length.*—0.15 cm.
*Anther shape.*—Ovoid.
*Color of pollen.*—RHS N187C.
*Pollen amount.*—Moderate.
*Fertility/seed set.*—Has not been observed on this hybrid.

Disease/pest resistance: Disease/pest resistance has not been observed on this hybrid.

What is claimed is:

1. A new and distinct variety of *Petunia* plant named 'PEHY0001' substantially as illustrated and described herein.

* * * * *

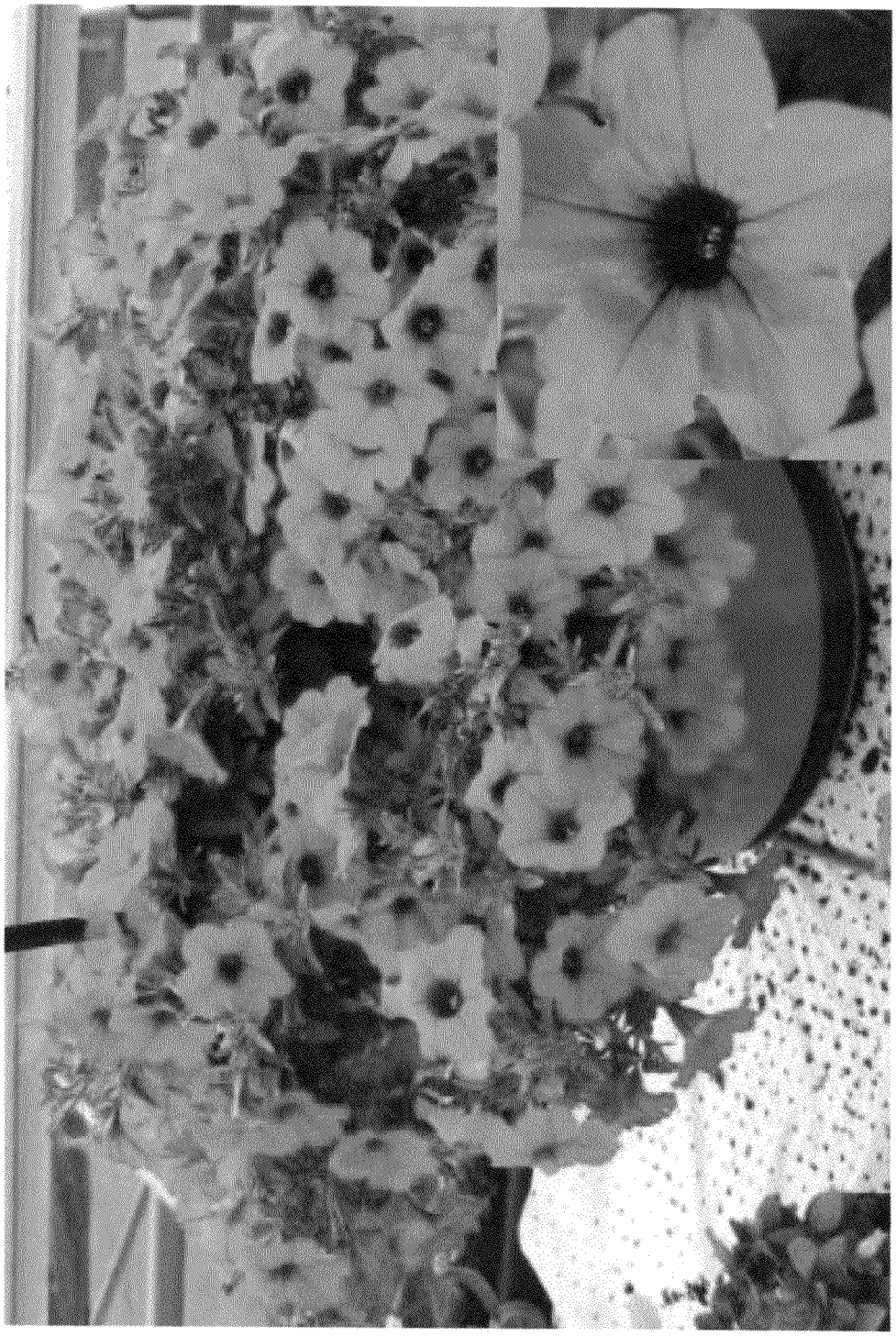

UNITED STATES PATENT AND TRADEMARK OFFICE

CERTIFICATE OF CORRECTION

PATENT NO. : PP23,599 P2
APPLICATION NO. : 13/317475
DATED : May 14, 2013
INVENTOR(S) : Hanes It is certified that error appears in the above-identified patent and that said Letters Patent is hereby corrected as shown below:

In the Specifications:

At column 1, line 28, delete "the" before --March 2008--

At column 2, line 30, delete "and" before --were taken--

At column 4, line 34-35, delete "RHS 83B and RHS 83B" and insert therefor --RHS 83A and RHS 83B--

Signed and Sealed this
Twenty-fifth Day of June, 2013

Teresa Stanek Rea
*Acting Director of the United States Patent and Trademark Office*